United States Patent
Bhunia et al.

(10) Patent No.: US 10,624,559 B2
(45) Date of Patent: Apr. 21, 2020

(54) FALL PREDICTION SYSTEM AND METHOD OF USING THE SAME

(71) Applicant: Starkey Laboratories, Inc., Eden Prairie, MN (US)

(72) Inventors: Sourav K. Bhunia, Shoreview, MN (US); Justin R. Burwinkel, Eden Prairie, MN (US); Jason A. Galster, Minneapolis, MN (US); Buye Xu, Eden Prairie, MN (US); Peter J. Tetrick, Chaska, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 0 days.

(21) Appl. No.: 15/858,630

(22) Filed: Dec. 29, 2017

(65) Prior Publication Data

US 2018/0228404 A1 Aug. 16, 2018

Related U.S. Application Data

(60) Provisional application No. 62/458,436, filed on Feb. 13, 2017.

(51) Int. Cl.
*G08B 23/00* (2006.01)
*A61B 5/11* (2006.01)
(Continued)

(52) U.S. Cl.
CPC ............. *A61B 5/1117* (2013.01); *A61B 3/113* (2013.01); *A61B 5/0002* (2013.01);
(Continued)

(58) Field of Classification Search
CPC ... A61B 5/1117; A61B 5/6816; A61B 5/6817; A61B 5/0002; A61B 2562/0219
(Continued)

(56) References Cited

U.S. PATENT DOCUMENTS 6,326,918 B1   12/2001   Stewart
6,647,257 B2   11/2003   Owensby
(Continued)

FOREIGN PATENT DOCUMENTS

EP    0799597 A1   10/1997
EP    1229508 A1    8/2002
(Continued)

OTHER PUBLICATIONS

U.S. Appl. No. 15/589,298, filed May 8, 2017, Burwinkel et al.
(Continued)

*Primary Examiner* — Tanmay K Shah
(74) *Attorney, Agent, or Firm* — Pauly, DeVries Smith & Deffner LLC

(57) ABSTRACT

Various embodiments of a fall prediction system and method of using such system are disclosed. The system includes a hearing device for a wearer, a sensor operatively connected to the hearing device and adapted to detect a characteristic of the wearer and generate a sensor signal based on the characteristic, and a controller operatively connected to the hearing device. The controller is adapted to determine a fall risk value based on the sensor signal, compare the fall risk value to a fall risk threshold, and generate a fall prevention output if the fall risk value exceeds the fall risk threshold.

19 Claims, 5 Drawing Sheets

(51) Int. Cl.
| | |
|---|---|
| A61B 5/00 | (2006.01) |
| G01S 19/19 | (2010.01) |
| G08B 21/04 | (2006.01) |
| G16H 50/30 | (2018.01) |
| G16H 40/60 | (2018.01) |
| H04R 25/00 | (2006.01) |
| A61B 3/113 | (2006.01) |

(52) U.S. Cl.
CPC .......... *A61B 5/0004* (2013.01); *A61B 5/1114* (2013.01); *A61B 5/4836* (2013.01); *A61B 5/6815* (2013.01); *A61B 5/6816* (2013.01); *A61B 5/6817* (2013.01); *A61B 5/7275* (2013.01); *A61B 5/742* (2013.01); *A61B 5/7405* (2013.01); *A61B 5/7455* (2013.01); *G01S 19/19* (2013.01); *G08B 21/0446* (2013.01); *G16H 40/60* (2018.01); *G16H 50/30* (2018.01); *H04R 25/305* (2013.01); *H04R 25/554* (2013.01); *A61B 2562/0219* (2013.01); *H04R 2225/55* (2013.01); *H04R 2460/07* (2013.01)

(58) Field of Classification Search
USPC ...................................................... 340/573.1
See application file for complete search history.

(56) References Cited

U.S. PATENT DOCUMENTS

| | | | |
|---|---|---|---|
| 6,816,878 | B1 | 11/2004 | Zimmers et al. |
| 6,836,667 | B1 | 12/2004 | Smith, Jr. |
| 7,007,327 | B2 | 3/2006 | Ogawa et al. |
| 7,139,820 | B1 | 11/2006 | O'Toole, Jr. et al. |
| 7,411,493 | B2 | 8/2008 | Smith |
| 7,450,954 | B2 | 11/2008 | Randall |
| 7,602,930 | B2 | 10/2009 | Kasztelan |
| 7,742,774 | B2 | 6/2010 | Oh et al. |
| 7,899,621 | B2 | 3/2011 | Breed et al. |
| 8,092,398 | B2 | 1/2012 | Weinberg et al. |
| 8,150,044 | B2 | 4/2012 | Goldstein et al. |
| 8,169,938 | B2 | 5/2012 | Duchscher et al. |
| 8,308,665 | B2 | 11/2012 | Harry et al. |
| 8,442,245 | B2 | 5/2013 | Wurzbacher et al. |
| 8,452,273 | B1 | 5/2013 | Khomenko et al. |
| 8,559,914 | B2 | 10/2013 | Jones |
| 8,652,040 | B2 | 2/2014 | Leboeuf et al. |
| 8,737,951 | B2 | 5/2014 | Jones et al. |
| 9,049,558 | B2 | 6/2015 | Jones et al. |
| 9,149,222 | B1 | 10/2015 | Zets et al. |
| 9,167,356 | B2 | 10/2015 | Higgins et al. |
| 9,179,862 | B2 | 11/2015 | Stergiou et al. |
| 9,216,132 | B2 | 12/2015 | Aoki et al. |
| 9,226,706 | B2 | 1/2016 | Uehara et al. |
| 9,426,582 | B2 | 8/2016 | Pontoppidan |
| 9,452,101 | B2 | 9/2016 | Tomlinson et al. |
| 9,848,273 | B1 | 12/2017 | Helwani et al. |
| 9,877,668 | B1 | 1/2018 | Sarkar et al. |
| 9,918,663 | B2 | 3/2018 | Singhatat |
| 9,936,916 | B2 | 4/2018 | Sahin |
| 10,149,798 | B2 | 12/2018 | Roth |
| 10,178,970 | B2 | 1/2019 | Oddsson et al. |
| 10,242,590 | B2 | 3/2019 | Yu |
| 10,271,790 | B2 | 4/2019 | Lee |
| 2005/0240378 | A1 | 10/2005 | Smith et al. |
| 2006/0251334 | A1 | 11/2006 | Oba et al. |
| 2006/0282021 | A1 | 12/2006 | DeVaul et al. |
| 2007/0197881 | A1 | 8/2007 | Wolf et al. |
| 2008/0129518 | A1 | 6/2008 | Carlton-Foss |
| 2009/0299622 | A1 | 12/2009 | Denaro |
| 2009/0322513 | A1 | 12/2009 | Hwang et al. |
| 2010/0010832 | A1 | 1/2010 | Boute et al. |
| 2010/0141439 | A1 | 6/2010 | Lunner |
| 2010/0179389 | A1 | 7/2010 | Moroney, III et al. |
| 2012/0092156 | A1 | 4/2012 | Tran |
| 2012/0101411 | A1* | 4/2012 | Hausdorff ............. A61B 5/1117 600/595 |
| 2013/0065569 | A1 | 3/2013 | Leipzig et al. |
| 2013/0091016 | A1 | 4/2013 | Shutter |
| 2013/0135097 | A1 | 5/2013 | Doezema |
| 2013/0343585 | A1 | 12/2013 | Bennett et al. |
| 2014/0023216 | A1 | 1/2014 | Solum et al. |
| 2014/0064528 | A1 | 3/2014 | Flood et al. |
| 2014/0074180 | A1 | 3/2014 | Heldman et al. |
| 2014/0266988 | A1 | 9/2014 | Fisher et al. |
| 2015/0018724 | A1 | 1/2015 | Hsu et al. |
| 2015/0209212 | A1 | 7/2015 | Duguid |
| 2015/0319546 | A1 | 11/2015 | Sprague |
| 2015/0351690 | A1 | 12/2015 | Toth et al. |
| 2016/0029938 | A1 | 2/2016 | Shudo |
| 2016/0070122 | A1 | 3/2016 | Sales et al. |
| 2016/0262608 | A1 | 9/2016 | Krueger |
| 2016/0263437 | A1 | 9/2016 | Kow et al. |
| 2016/0275805 | A1 | 9/2016 | Reichow |
| 2017/0006931 | A1* | 1/2017 | Guez .................... A61B 5/0476 |
| 2017/0116846 | A1 | 4/2017 | Wengrovitz et al. |
| 2017/0127196 | A1 | 5/2017 | Blum et al. |
| 2017/0140637 | A1 | 5/2017 | Thurlow et al. |
| 2017/0188895 | A1 | 7/2017 | Nathan |
| 2017/0197115 | A1 | 7/2017 | Cook et al. |
| 2017/0229041 | A1 | 8/2017 | Reichow et al. |
| 2017/0273616 | A1 | 9/2017 | Yang et al. |
| 2017/0291065 | A1 | 10/2017 | Klopman |
| 2018/0092572 | A1 | 4/2018 | Sanchez et al. |
| 2018/0093121 | A1 | 4/2018 | Matsuura et al. |
| 2018/0242859 | A1 | 8/2018 | Leboeuf et al. |
| 2018/0250494 | A1 | 9/2018 | Hanbury |
| 2018/0279915 | A1 | 10/2018 | Huang et al. |
| 2018/0279919 | A1 | 10/2018 | Bansbach et al. |
| 2018/0289287 | A1 | 10/2018 | Sio et al. |
| 2019/0117121 | A1 | 4/2019 | Kutina et al. |

FOREIGN PATENT DOCUMENTS

| | | |
|---|---|---|
| EP | 1628504 A2 | 2/2006 |
| EP | 2104366 A2 | 9/2009 |
| EP | 1983896 | 6/2017 |
| EP | 3328277 | 6/2018 |
| WO | WO 2009/053184 A1 | 9/2009 |
| WO | WO 2010/046504 A2 | 4/2010 |
| WO | WO 2010/049543 A2 | 5/2010 |
| WO | WO 2010/108287 A1 | 9/2010 |
| WO | WO 2012/083102 A1 | 6/2012 |
| WO | 2015164456 | 10/2015 |
| WO | 2016097746 | 6/2016 |
| WO | WO 2016/088027 A1 | 6/2016 |
| WO | WO 2016/110804 A1 | 7/2016 |
| WO | WO 2016/123129 A1 | 8/2016 |
| WO | 2018223505 | 12/2018 |
| WO | 2019073473 | 4/2019 |
| WO | 2019086997 | 5/2019 |

OTHER PUBLICATIONS

U.S. Appl. No. 15/858,680, filed Dec. 29, 2017, Burwinkel et al.
U.S. Appl. No. 15/895,311, filed Feb. 13, 2018, Burwinkel et al.
Barber & Stockwell, "Manual of Electronystagmography," 1980, C.V. Mosby Company, St. Louis, Missouri, Cover page, copyright page, and table of contents; total of 3 pages.
Buatois et al., "Posturography and risk of recurrent falls in healthy non-institutionalized persons aged over 65," *Gerontology*, 2006; 52(6):345-352.
Da Costa et al., "Can falls risk prediction tools correctly identify fall-prone elderly rehabilitation inpatients? A systematic review and meta-analysis," *PLoS One*, 2012; 7(7):e41061.
El Miedany et al., "Falls risk assessment score (FRAS): Time to rethink," *Journal of Clinical Gerontology & Geriatrics*, 2011; 2(1):21-26.
Horak, "Postural orientation and equilibrium: what do we need to know about neural control of balance to prevent falls?" *Age and Ageing*, 2006; 35-S2:ii7-ii11.

(56) References Cited

OTHER PUBLICATIONS

Howcroft et al., "Understanding dynamic stability from pelvis accelerometer data and the relationship to balance and mobility in transtibial amputees," *Gait Posture*, 2015; 41(3):808-812.

Howcroft et al., "Review of fall risk assessment in geriatric populations using inertial sensors," *J Neuroeng Rehab*, 2013; 10:91.

International Search Report and Written Opinion for PCT application No. PCT/US2017/069026, dated Apr. 3, 2018, 14 pages.

International Search Report and Written Opinion for PCT application No. PCT/US2017/069035, dated Apr. 3, 2018, 14 pages.

International Search Report and Written Opinion for PCT application No. PCT/US2018/017944, dated Apr. 26, 2018, 10 pages.

Marschollek et al., "Predicting in-patient falls in a geriatric clinic: a clinical study combining assessment data and simple sensory gait measurements," *Z Gerontol Geriatr*, 2009; 42(4):317-321.

Oliver, "Falls risk-prediction tools for hospital inpatients. Time to put them to bed?" *Age and Ageing*, 2008; 37:248-250.

PathVU Mobile App, Pathway Accessibility Solutions, Inc., Pittsburgh, Pennsylvania [retrieved on Jun. 19, 2018. Retrieved from the Internet:<URL: http://www.pathvu.com/>; 6 pgs.

Rumalla et al., "The effect of hearing aids on postural stability," *Laryngoscope*, 2015; 125(3):720-723.

Viikki, "Machine Learning on Otoneurological Data: Decision Trees for Vertigo Diseases," Academic Dissertation, University of Tampere, Finland, 2002; 84 pages.

Yang et al., "Fall risk assessment and early-warning for toddler behaviors at home," *Sensors*, 2013; 13:16985-17005.

Klenk et al., "Conceptualizing a Dynamic Fall Risk Model Including Intrinsic Risks and Exposures," *JAMDA*, 2017; 18:921-927.

"International Preliminary Report on Patentability," for PCT Application No. PCT/US2017/069026 dated Aug. 22, 2019 (9 pages).

"International Preliminary Report on Patentability," for PCT Application No. PCT/US2017/0690365 dated Aug. 22, 2019 (9 pages).

"International Preliminary Report on Patentability," for PCT Application No. PCT/US2018/017944 dated Aug. 22, 2019 (7 pages).

"Non-Final Office Action," for U.S. Appl. No. 15/858,680 dated Jan. 16, 2020 (25 pages).

\* cited by examiner

FALL PREDICTION SYSTEM AND METHOD OF USING THE SAME

CROSS-REFERENCE TO RELATED APPLICATION

This application claims priority to U.S. Provisional Patent Application No. 62/458,436, filed Feb. 13, 2017, which is incorporated herein by reference.

BACKGROUND

Maintaining postural control and preventing a fall are of importance for the elderly. Falls are the second leading cause of accidental or unintentional injury deaths worldwide, and are especially prevalent in the elderly. Currently, individuals are often inadequately prepared to protect themselves from falls or other serious injuries as the onset of such events may come without perceptible warning. Further, maintaining postural equilibrium, i.e., prevention of a fall, involves stabilization of the body's center of mass during both self-initiated and externally triggered disturbances to postural stability during normal daily activities. Maintaining such equilibrium can be accomplished by limiting the motion of the center of mass within the base of support formed by and around the feet. Postural equilibrium is maintained through multisensory inputs. For example, loss of sensory input in the feet due to neuropathy can increase the risk of a fall, even though the necessary motor control for a corrective action of repositioning the feet may still be intact.

Differential diagnosis of balance-related conditions often takes weeks or longer and can become especially costly to perform. A typical balance-related evaluation can last 1-2 hours and require a clinician to induce symptoms of imbalance, which can be especially uncomfortable for the patient as they may begin to feel dizzy and nauseous. Further, many patients do not have complete recollection of the events leading up to and during a period of spontaneous imbalance or a fall. In addition, adherence to postural training provided by healthcare specialists is not easily monitored during normal daily activities outside of the training facility.

SUMMARY

In general, the present disclosure provides various embodiments of a fall prediction system and a method of utilizing such system. The fall prediction system can include a hearing device and one or more sensors operatively connected to the device. The one or more sensors are adapted to detect one or more characteristics of a wearer of the device and generate one or more sensor signals based on the characteristic. The characteristic can be any suitable characteristic of the wearer, including at least one of a physiological characteristic and an environmental characteristic of the wearer. A controller of the system can be adapted to determine a fall risk value based on the sensor signal, compare the fall risk value to a fall risk threshold, and generate a fall prevention signal if the fall risk value exceeds the fall risk threshold.

In one aspect, the present disclosure provides a fall prediction system that includes a hearing device for a wearer, a sensor operatively connected to the hearing device and adapted to detect a characteristic of the wearer and generate a sensor signal based on the characteristic, where the characteristic includes at least one of a physiological characteristic and an environmental characteristic of the wearer; and a controller operatively connected to the hearing device. The controller is adapted to determine a fall risk value based on the sensor signal, compare the fall risk value to a fall risk threshold, and generate a fall prevention output if the fall risk value exceeds the fall risk threshold.

In another aspect, the present disclosure provides a method that includes detecting a characteristic of a wearer of a fall prediction system with a sensor, where the fall prediction system includes a hearing device, and further where the characteristic includes at least one of a physiological characteristic and an environmental characteristic; and determining a fall risk value based on the detected characteristic. The method further includes determining a fall risk threshold, and comparing the fall risk value to the fall risk threshold.

All headings provided herein are for the convenience of the reader and should not be used to limit the meaning of any text that follows the heading, unless so specified.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements.

The words "preferred" and "preferably" refer to embodiments of the disclosure that may afford certain benefits, under certain circumstances; however, other embodiments may also be preferred, under the same or other circumstances. Furthermore, the recitation of one or more preferred embodiments does not imply that other embodiments are not useful, and is not intended to exclude other embodiments from the scope of the disclosure.

In this application, terms such as "a," "an," and "the" are not intended to refer to only a singular entity, but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

These and other aspects of the present disclosure will be apparent from the detailed description below. In no event, however, should the above summaries be construed as limitations on the claimed subject matter, which subject matter is defined solely by the attached claims, as may be amended during prosecution.

BRIEF DESCRIPTION OF THE DRAWINGS

Throughout the specification, reference is made to the appended drawings, where like reference numerals designate like elements, and wherein.

DETAILED DESCRIPTION

Figure 1:
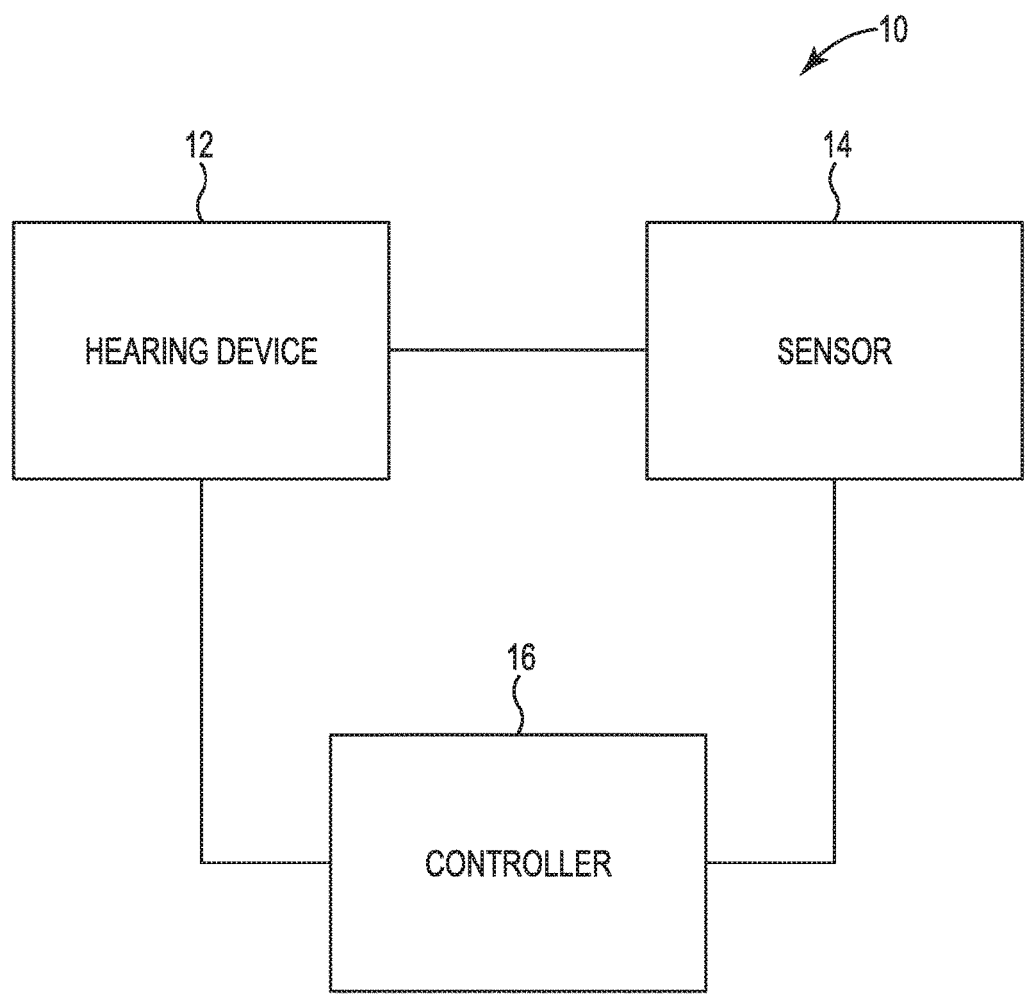
FIG. 1 is a schematic cross-section view of one embodiment of a fall prediction system.

In general, the present disclosure provides various embodiments of a fall prediction system and a method of utilizing such system. The fall prediction system can include a hearing device and one or more sensors operatively connected to the device. The one or more sensors are adapted to detect one or more characteristics of a wearer of the device and generate one or more sensor signals based on the characteristic. The characteristic can be any suitable characteristic of the wearer, including at least one of a physiological characteristic and an environmental characteristic. A controller of the system can be adapted to determine a fall risk value based on the sensor signal, compare the fall risk value to a fall risk threshold, and generate a fall prevention signal if the fall risk value exceeds the fall risk threshold.

The fall prediction systems and methods described herein can be utilized to determine whether a wearer of such system or systems may have an increased probability of a fall. Further, one or more embodiments of a fall prediction system described herein can provide one or more outputs that can prevent the wearer of the system from falling. One or more embodiments of a fall prediction system described herein can also be utilized to determine whether the wearer of the device has experienced a fall.

Any suitable technique or techniques can be utilized with the described embodiments of fall prediction systems. For example, in one or more embodiments, a fall prediction system can include one or more sensors to detect, predict, and prevent its wearer from falling. Such sensors can include, e.g., one or more of a microphone, loudspeaker, accelerometer, barometer, magnetometer, a gyroscope, electrode sensor, (e.g., for EOG, EKG, galvanic skin response) and an optical sensor. In one or more embodiments, an accelerometer can be utilized with one or both of a magnetometer and gyroscope for fall prediction and detection. For example, detection of a fall of the wearer can be accomplished by detecting, e.g., the speed of change of posture while the relative orientation of both the system and the wearer remain the same, and body rotation of the wearer, etc. Postural stability can include detection of a fluctuation in a magnitude and direction of acceleration as the wearer goes about daily activities. Such detection can also include day-to-day variations in heart rate during comparable activities. Both the long-term and short-term risks of a fall can be predicted. In general, the long-term risk is the probability of falling based on the wearer's long-term history of health, motion, physiological patterns, etc. Further, the short-term fall risk can indicate the fall risk at the moment based on the current physiological status of the wearer and the environment proximate the wearer (e.g., slippery floors).

In one or more embodiments, the fall prediction system can include one or more sensors that measure eye movement (i.e., electrooculography (EOG) measurements). For example, the system can include one or more EOG sensors for the tracking of eye movement and nystagmus. In one or more embodiments, the system can also include a positional sensor that may be utilized to correlate EOG sensor data. Data from the EOG sensors and positional sensors can be utilized to detect peripheral vestibular asymmetry (which can cause nystagmus and feelings of imbalance/dizziness to occur).

Parallel positional sensors that can be provided by a fall prediction system and that include a binaural set of hearing devices can also be used to detect falls. Further, the use of two separate, but parallel, positional sensors can provide a redundant system that can prevent false-positive fall detection.

Any suitable fall prediction system or device can be utilized for fall prediction, prevention, and/or detection. For example, FIG. 1 is a schematic cross-section view of one embodiment of a fall prediction system 10. The fall prediction system 10 includes a hearing device 12 for a wearer, a sensor 14 operatively connected to the hearing device, and a controller 16 operatively connected to one or both of the hearing device and the controller. As used herein, the term "operatively connected" means that an element or component can be connected to another element or component using any suitable technique or techniques such that information can be shared between such components. In one or more embodiments, the sensor 14 can be operatively connected to the hearing device 12 by a wire or cable, wirelessly using any suitable wireless protocol, optically, etc.

The sensor 14 is adapted to detect a characteristic of the wearer, e.g., at least one of a physiological characteristic and an environmental characteristic, and generate a sensor signal based on such characteristic. In one or more embodiments, the controller 16 is adapted to determine a fall risk value based on the sensor signal, compare the fall risk value to a fall risk threshold, and generate a fall prevention output if the fall risk value exceeds the fall risk threshold as is further described herein. In one or more embodiments, the controller 16 can be adapted to determine a second fall risk value based on the sensor signal, compare the second fall risk value to a second fall risk threshold, and generate a second fall prevention output if the second fall risk value exceeds the second fall risk threshold. In one or more embodiments, the controller 16 can be adapted to determine any suitable number of risk values and compare those values to any suitable number of fall risk thresholds.

The system 10 can include any suitable hearing device 12 for a wearer, including but not limited to, a wearable hearing device such as headphones. In one or more embodiments, the hearing device can include a hearing aid such as behind-the-ear (BTE), in-the-ear (ITE), in-the-canal (ITC), or completely-in-the-canal (CIC) type hearing aid. It is understood that behind-the-ear type hearing aids may include devices that reside substantially behind the ear or over the ear. Such devices may include hearing aids with receivers associated with the electronics portion of the behind-the-ear device, or hearing aids of the type having receivers in the ear canal of the wearer. Such devices are also known as receiver-in-the-canal (RIC) or receiver-in-the-ear (RITE) hearing devices. In one or more embodiments, the hearing device 12 can include a cochlear implant (including its processor) or a bone-conduction or otherwise osseointegrated hearing device. It is understood that other hearing devices not expressly stated herein may fall within the scope of the present subject matter. While depicted as including one hearing device 12, the system 10 can include two or more hearing devices. For example, in one or more embodiments, the system 10 can include a left hearing device that is adapted to be acoustically connected to the wearer's left ear and a right hearing device that is adapted to be acoustically connected to the wearer's right ear.

Figure 2:
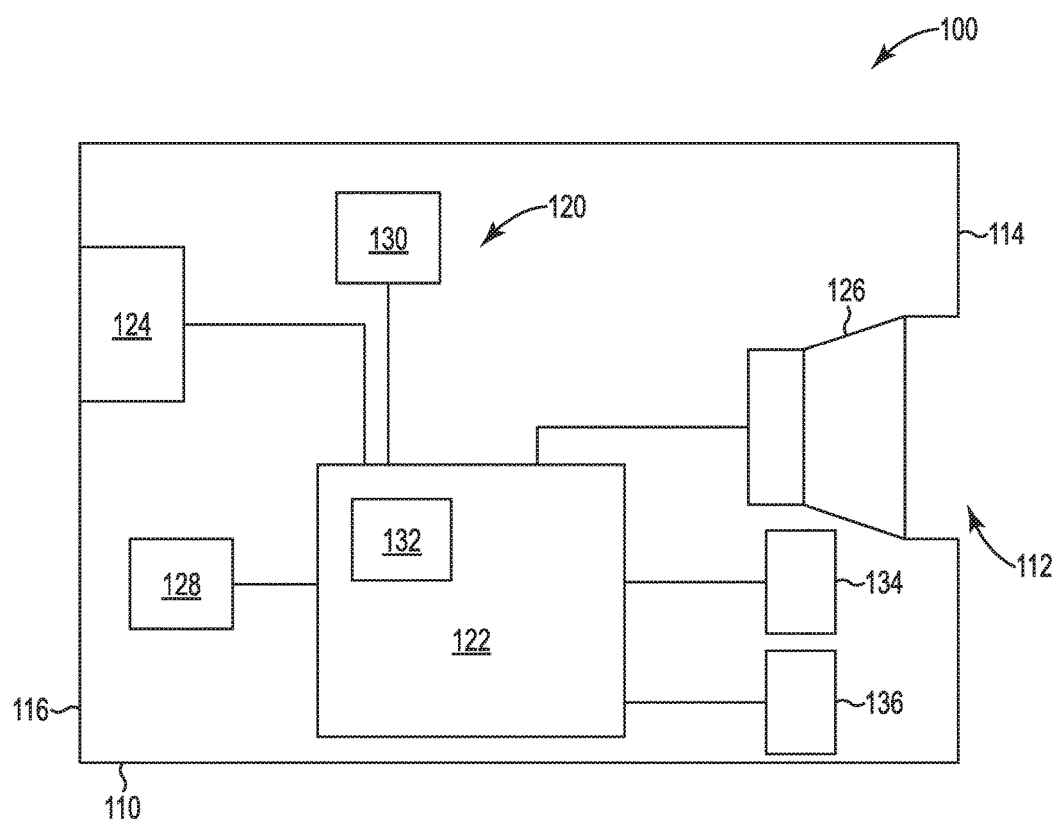
FIG. 2 is a schematic cross-section view of one embodiment of a hearing device that can be utilized with the fall prediction system of FIG. 1.

The hearing device 12 can include any suitable hearing assistance components. For example, FIG. 2 is a schematic cross-section view of one embodiment of a hearing device 100. The device 100 includes a housing 110 and hearing assistance components 120 disposed within the housing. Hearing assistance components 120 can include any suitable device or devices, e.g., integrated circuits, power sources, microphones, receivers, etc. For example, in one or more embodiments, the components 120 can include a controller 122 (e.g., controller 16 of FIG. 1), a microphone 124, a receiver 126 (e.g., speaker), a power source 128, an antenna 130, and one or more sensors 134, 136 (e.g., sensor 14 of FIG. 1). The microphone 124, receiver 126, power source 128, antenna 130, and sensors 134, 136 can be electrically connected to the controller 122 using any suitable technique or techniques.

Any suitable controller 122 can be utilized with the hearing device 100, e.g., the same controller or controllers described regarding controller 16 of system 10 of FIG. 1. For example, the controller 122 can be adapted to employ programmable gains to adjust the hearing device output to a patient's particular hearing impairment. The controller 122 can be a digital signal processor (DSP), microprocessor, microcontroller, other digital logic, or combinations thereof. The processing can be done by a single processor, or can be distributed over different devices. The processing of signals referenced in this disclosure can be performed using the controller 122 or over different devices.

In one or more embodiments, the controller 122 is adapted to perform instructions stored in one or more memories 132. Various types of memory can be used, including volatile and nonvolatile forms of memory. In one or more embodiments, the controller 122 or other processing devices execute instructions to perform a number of signal processing tasks. Such embodiments can include analog components in communication with the controller 122 to perform signal processing tasks, such as sound reception by the microphone 124, or playing of sound using the receiver 126.

In general, digital hearing devices include a controller or processor. In such devices, programmable gains may be employed to adjust the hearing device output to a wearer's particular hearing impairment. The controller 122 (and controller 16 of FIG. 1) may be a digital signal processor (DSP), microprocessor, microcontroller, other digital logic, or combinations thereof. The processing may be performed by a single processor, or may be distributed over different devices. The processing of signals referenced in this application can be performed using the processor or other different devices. Processing may be done in the digital domain, the analog domain, or combinations thereof. Processing may be done using subband processing techniques. Processing may be done using frequency domain or time domain approaches. Some processing may involve both frequency and time domain aspects. For brevity, in some examples drawings may omit certain blocks that perform frequency synthesis, frequency analysis, analog-to-digital conversion, digital-to-analog conversion, amplification, buffering, and certain types of filtering and processing. In various embodiments, the processor is adapted to perform instructions stored in one or more memories, which may or may not be explicitly shown. Various types of memory may be used, including volatile and nonvolatile forms of memory. In various embodiments, the processor or other processing devices execute instructions to perform a number of signal processing tasks. Such embodiments may include analog components in communication with the processor to perform signal processing tasks, such as sound reception by a microphone, or playing of sound using a receiver (i.e., in applications where such transducers are used). In various embodiments, different realizations of the block diagrams, circuits, and processes set forth herein can be created by one of skill in the art without departing from the scope of the present subject matter.

The hearing assistance components 120 can also include the microphone 124 that is electrically connected to the controller 122. Although one microphone 124 is depicted, the components 120 can include any suitable number of microphones. Further, the microphone 124 can be disposed in any suitable location within the housing 110. For example, in one or more embodiments, a port or opening can be formed in the housing 110, and the microphone 124 can be disposed adjacent the port to receive audio information from the wearer's environment.

Any suitable microphone 124 can be utilized. In one or more embodiments, the microphone 124 can be selected to detect one or more audio signals and convert such signals to an electrical signal that is provided to the controller 122. Although not shown, the controller 122 can include an analog-to-digital convertor that converts the electrical signal from the microphone 124 to a digital signal.

Electrically connected to the controller 122 is the receiver 126. Any suitable receiver can be utilized. In one or more embodiments, the receiver 126 can be adapted to convert an electrical signal from the controller 122 to an acoustic output or sound that can be transmitted from the housing 110 to the wearer. In one or more embodiments, the receiver 126 can be disposed adjacent an opening 112 disposed in a first end 114 of the housing 110. As used herein, the term "adjacent the opening" means that the receiver 126 is disposed closer to the opening 112 in the first end 114 than to a second end 116 of the housing 110.

The power source 128 is electrically connected to the controller 122 and is adapted to provide electrical energy to the controller and one or more of the other hearing assistance components 120. The power source 128 can include any suitable power source or power sources, e.g., a battery. In one or more embodiments, the power source 128 can include a rechargeable battery. In one or more embodiments, the components 120 can include two or more power sources 128.

The components 120 can also include the optional antenna 130. Any suitable antenna or combination of antennas can be utilized. In one or more embodiments, the antenna 130 can include one or more antennas having any suitable configuration. For example, antenna configurations can vary and can be included within the housing 110 or be external to the housing. Further, the antenna 130 can be compatible with any suitable protocol or combination of protocols. In one or more embodiments, the components 120 can also include a transmitter that transmits electromagnetic signals and a radio-frequency receiver that receives electromagnetic signals using any suitable protocol or combination of protocols.

For example, in one or more embodiments, the hearing device 100 can be connected to one or more external devices using, e.g., Bluetooth, Wi-Fi, magnetic induction, etc. For example, in one or more embodiments, the hearing device 100 can be wirelessly connected to the Internet using any suitable technique or techniques. Such connection can enable the hearing device 100 to access any suitable databases, including medical records databases, cloud computing databases, location services, etc. In one or more embodiments, the hearing device 100 can be wirelessly connected utilizing the Internet of Things (IoT) such that the hearing device can communicate with, e.g., hazard beacons, one or more cameras disposed in proximity to the wearer, motion sensors, room lights, etc. Further, in one or more embodiments, the hearing device 100 can access weather information via the Internet using any suitable technique or techniques such that the wearer can be informed of potentially hazardous weather conditions.

In one or more embodiments, the hearing device 100 can include the first sensor 134 and the second sensor 136. Although depicted as including two sensors 134, 136, the hearing device 100 can include any suitable number of sensors, e.g., 1, 2, 3, 4, 5, or more sensors. The sensors 134, 136 can include any suitable sensor or sensors, e.g., the same sensors described herein regarding sensor 14 of system 10 of FIG. 1. The first sensor 134 can include the same sensor as the second sensor 136. In one or more embodiments, the first sensor 134 includes a sensor that is different from that of the second sensor 136. The sensors 134, 136 can be operatively connected to the controller 122 using any suitable technique or techniques.

In one or more embodiments, first sensor 134 is operatively connected to the hearing device 100 and adapted to detect a first characteristic of the wearer and generate a sensor signal based on the first characteristic. In one or more embodiments, the second sensor 136 is operatively connected to the hearing device 100 and adapted to detect a second characteristic of the wearer and generate a second sensor signal based on the second characteristic. The first and second characteristic of the wearer can be any suitable characteristic, e.g., at least one of a physiological characteristic and an environmental characteristic of the wearer. The controller 122 can be adapted to determine a fall risk value based on the sensor signal from the first sensor 134 and the second sensor signal from the second sensor 136. The first and second characteristics can include any suitable characteristic, e.g., the same characteristic or characteristics described herein regarding sensor 14 of system 10 of FIG. 1. The characteristic detected by the first sensor 134 can be the same as or different from the second characteristic detected by the second sensor 136. For example, in one or more embodiments, the characteristic detected by the first sensor 134 can be eye movement of the wearer and the second characteristic detected by the second sensor 136 can be head movement of the wearer. In such embodiments, the controller 122 can be adapted to determine the fall risk threshold by measuring a maximum displacement between a longitudinal axis of the wearer and a normal to the earth's surface as a function of time based on the second sensor signal 136. In one or more embodiments, the controller 122 can be adapted to determine the fall risk threshold by measuring a maximum velocity of displacement between a longitudinal axis of the wearer and a normal to the earth's surface based on the second sensor signal.

Returning to FIG. 1, the sensor 14 is operatively coupled to the hearing device 12. The sensor 14 can be operatively coupled to the device 12 using any suitable technique or techniques, e.g., electrical, optical, or wireless coupling. The sensor 14 can be disposed in any suitable location. In one or more embodiments, the sensor 14 can be a component of hearing assistance components of the hearing device 12, e.g., such as sensors 134, 136 of hearing assistance components 120 of FIG. 2. In one or more embodiments, one or more sensors 14 can be disposed outside of the housing of the hearing device 12 and operatively coupled to the device and the controller 16 using any suitable technique or techniques. In one or more embodiments, one or more sensors 14 can be disposed within one or both ears and outside the ear of the wearer.

The sensor 14 can include any suitable sensor or sensors. For example, the sensor 14 can include at least one of an accelerometer, barometer, gyroscope, heart rate sensor, blood pressure sensor, magnetometer, eye sensor, EEG sensor, blood sugar sensor, light sensor, sweat sensor, pupillometry sensor, cerumen sensor, cortisol sensor, body temperature sensor, humidity sensor, air quality sensor, and combinations thereof. The sensor 14 can be adapted to detect any suitable characteristic of the wearer, e.g., at least one of a physiological characteristic and an environmental characteristic of the wearer. For example, the physiological characteristic can include at least one of body position, eye movement, body temperature, heart rate, EEG, skin impedance, and combinations thereof.

Further, in one or more embodiments, the sensor 14 can be adapted to detect one or more environmental or ambient characteristics proximate to the wearer of the hearing device 12. For example, such sensor 14 can include at least one of an ambient temperature sensor, barometer, microphone, GPS sensor, moisture/humidity sensor, image sensor (i.e., a camera), and combinations thereof. The sensor 14 can be adapted to detect any suitable environmental characteristic or characteristics, e.g., temperature, moisture/humidity, sound, light intensity, terrain, elevation, ambient oxygen levels, pollutants, toxins, carbon monoxide levels, and combinations thereof.

Operatively connected to the hearing device 12 is the controller 16. In one or more embodiments, the controller 16 can also be operatively connected to the sensor 14. The controller 16 can include any suitable controller or controllers, e.g., the same controller described regarding controller 122 of the hearing device 100 of FIG. 2. The controller 16 can be disposed in any suitable location relative to the hearing device 10 and the sensor 14. In one or more embodiments, the controller 16 is disposed within the housing of the hearing device 12, e.g., within housing 110 of hearing device 100 of FIG. 2. In one or more embodiments, the controller 16 can be disposed external to the hearing device 12, e.g., the hearing device can be wirelessly connected to the wearer's smart phone or computer using any suitable technique or techniques. In one or more embodiments, the controller 16 can include a first controller disposed within the hearing device 12 and a second or additional controllers disposed externally to the hearing device.

Figure 3:
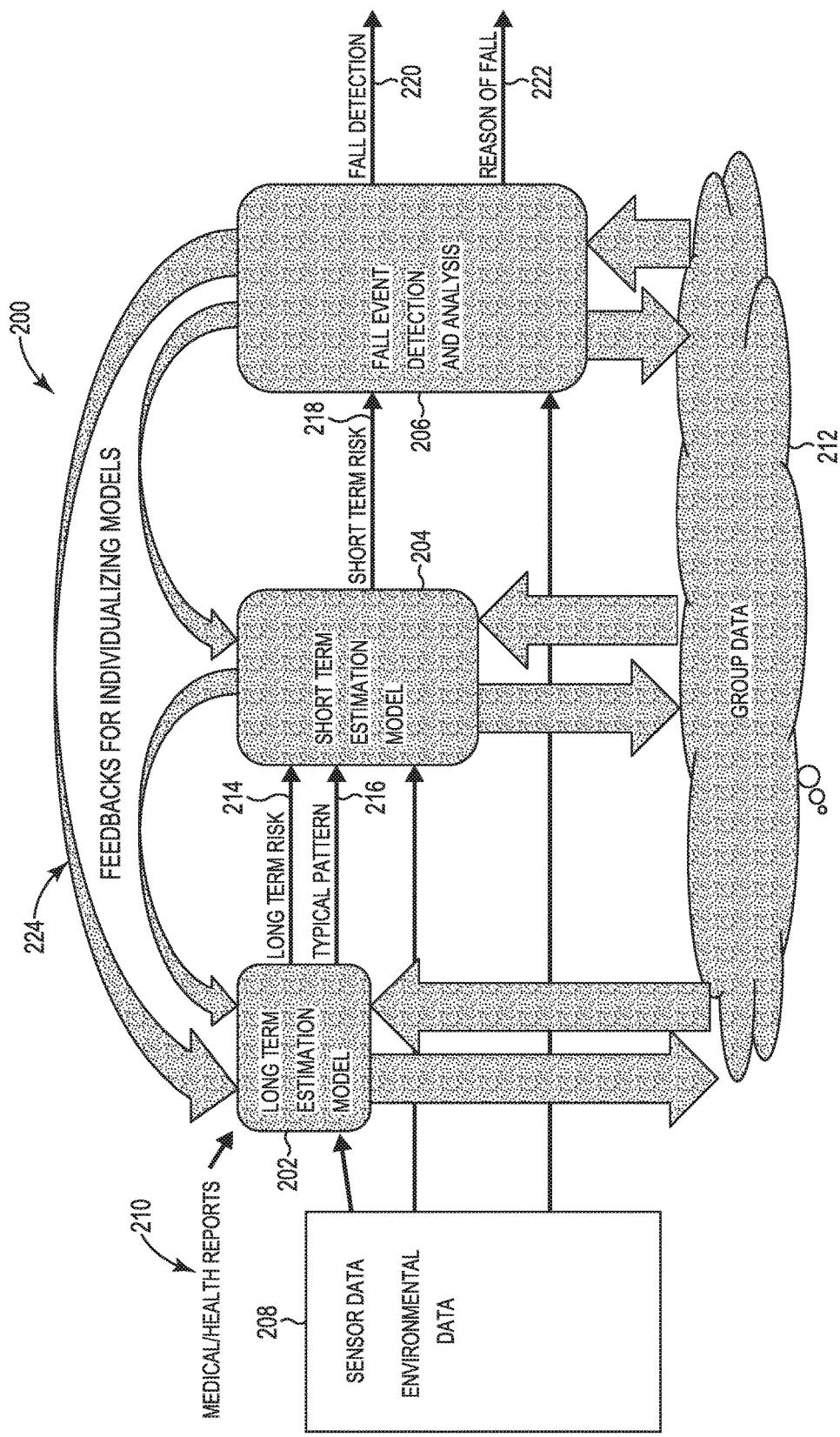
FIG. 3 is a flow chart of one embodiment of a method of utilizing the fall prediction system of FIG. 1.

The controller 16 can be adapted to perform any suitable function or functions to process inputs from any suitable source or sources and provide an estimation of the risk of a fall. In one or more embodiments, the controller 16 can be adapted to detect falls. For example, FIG. 3 is a flow chart of one embodiment of a method 200 of predicting and detecting a fall event. Although described in regard to the fall prediction system 10 of FIG. 1, the method 200 can be utilized with any suitable system or device. In one or more embodiments, the method 200 includes generating a long-term fall estimation model 202, generating a short-term fall estimation model 204, and detecting a fall event 206.

For generating one or more of the long-term fall estimation model 202, the short-term fall estimation model 204, and the fall event detection 206, a risk or probability value of a fall can be based on a predetermined formula or formulas that can be derived from experimental data. The formula can also be entirely learned or modified through various machine learning approaches. For example, when a fall event is detected at 206, the method 200 can send data collected before the event by one or more sensors 14, e.g., to a cloud server 212. In one or more embodiments, data from the wearer and other wearers can be used to train a regression model or deep neural network to estimate the risk of a fall for an individual wearer.

At each stage 202, 204, 206, different actions can be taken or outputs provided to aid in preventing a fall or reducing the severity of a fall. For example, when a long-term risk value 214 generated by the long-term fall estimation model 202 is determined to exceed a fall prevention threshold, the system 10 can generate a fall prevention output that includes notifying one or more of the wearer, caregiver, and medical professional for proper diagnosis and treatment. When a short-term fall risk value 218 generated by the short-term estimation model 204 exceeds a fall prevention threshold, the system 10 can generate a fall prevention output that includes sending a warning signal to the wearer, increasing an intensity of the ambient light for the wearer's environment, notifying other IoT devices proximate to the wearer to help prevent the fall or otherwise protect the wearer from injury, etc. If a fall event is detected at 206, the system 10 can monitor the wearer's physiological characteristics, notify a caregiver, notify a medical professional, etc.

The long-term fall estimation model 202 can be generated from analytics or machine learning of larger group data using any suitable technique or techniques, e.g., regression, steady-state, Bayesian, classification trees, Volterra, support vector machine, Gaussian mixture, neural network techniques, and combinations thereof.

The long-term estimation model 202 can provide an estimate or probability of the general risk (or capability of keeping balance) of the wearer and learn the wearer's norms regarding motion patterns and health/physiological information. Inputs for generating the long-term fall estimation model 202 can either be obtained based on clinical evaluations and medical history, or be learned by the fall prediction system 10 from inputs provided by various types of sensors, e.g., sensor 14. For example, motion patterns of the wearer and changes to such patterns can be estimated and monitored based on the outputs from one or more of an inertial measurement unit (IMU) sensor, GPS sensor barometer, magnetometer, EEG sensor, camera, etc. The motion of the wearer may include sway amplitude and speed while walking, speed and trajectory when sitting down or standing up, speed and radius when turning, stride length, symmetry and variance, reaction speed, etc. In one or more embodiments, physiological characteristics that can be provided as inputs to the long-term estimation model 202 include heart rate, blood pressure, blood sugar, blood oxygen, core body temperature, etc., and can be monitored utilizing any suitable sensor or sensors 14. All such inputs and how they change over time can be monitored and used to estimate the long-term fall risk 214 (i.e., how prone the wearer is to a fall).

Any suitable inputs can be utilized to generate the long-term fall estimation model 202. For example, in one or more embodiments, data inputs 208 such as sensor data from one or more sensors (e.g., sensor 14) related to physiological characteristics of the wearer, environmental data regarding the environment proximate to the wearer (i.e., an environmental characteristic of the wearer), and combinations of physiological and environmental characteristics or data can be utilized by the long-term estimation model 202 to determine the fall risk value 214. Medical/health reports 210 regarding the wearer can also be provided as inputs to the long-term fall estimation model 202. Further, group data from the cloud 212 can also be provided as inputs to the long-term fall estimation model 202.

The method 200 further includes generating the short-term fall estimation model 204. In one or more embodiments, the model 204 can generate a short-term fall risk value or probability. Such short-term fall risk value 218 can be based on any suitable input or inputs. For example, in one or more embodiments, this risk value 218 can be based on the detection of one or more signature indicators, such as abnormal eye movement, sudden drop of blood pressure or blood sugar, abnormal heart rate, sudden increase of sway speed and amplitude, a quick change in elevation, ambient temperatures near freezing, etc. The seriousness of the detected inputs can be derived by comparing such inputs to averaged norms of the wearer's age group and then, together with certain environmental data, used to estimate the short-term fall risk value 218.

Further, typical patterns of the wearer can be provided as inputs 216 to the short-term fall estimation model 204. Such typical patterns 216 can be determined based upon various parameters, including gait, postural transitions, and general activity levels of the wearer. For example, the wearer's typical patterns 216 can be determined based upon, e.g., walking speed, cadence, gait symmetry and variance, step clearance, sway, speed of postural transitioning (how long it takes to stand up or sit down), total number of steps per day, number of transitions each day, number of walks per day, distance or duration of each walk on average, total walking distance per day, etc.

In one or more embodiments, the averaged group norms can be replaced by the values that are adjusted based on the wearer's normal behaviors that are learned when generating the long-term fall estimation model 202. The wearer's long-term fall risk value 214 can also be an input for the short-term fall estimation model 204 when generating the short-term fall risk value.

Various sensors 14 (e.g. IMU, barometer) can be used to detect a fall 220 at 206. The short-term and long-term fall risk values 214, 218 can also be incorporated to increase a confidence interval of the fall detection 206 and reduce false positives. In addition, physiological data collected before the fall event 220 can be used to help analyze a reason or reasons for the fall 222.

In one or more embodiments, the method 200 can include one or more feedback pathways 224 for individualizing one or more of the long-term fall estimation model 202 and the short-term fall estimation models 204.

Returning to FIG. 1, the fall prediction system 10 can be utilized to receive input information and determine the likelihood or probability that the wearer of the fall prediction system will fall. In one or more embodiments, the fall prediction system 10 can be utilized to receive input information from any suitable source to determine whether the wearer has fallen. The input information can be provided using any suitable sensor or device. For example, the input information can be provided to the controller 16 by the sensor 14, the hearing device 12, manually by one or more of the wearer, a caregiver, and a medical professional, or obtained from other systems via wired or wireless connections to system 10.

Further, the fall prediction system 10 can provide any suitable outputs that can be based on the probability of a fall or that a fall has occurred. Any suitable output or outputs can be provided by the system 10, e.g., notifications, reports, IoT triggers (e.g., activating room lighting), treatments to the wearer of the device 12, etc. In one or more embodiments, the system 10 can be utilized to detect head impact, check with the wearer for consciousness, and inform one or more of the wearer, caregiver, and medical professional of the detection of a head impact and level of consciousness of the wearer.

The fall prediction system 10 can utilize any suitable technique or techniques to determine the risk of a fall and/or that a fall has occurred. For example, in one or more embodiments, the controller 16 can be adapted to determine a fall risk value based on one or more inputs. The fall risk value can be any suitable value or scale that correlates to a probability that the wearer may experience a fall.

Further, any suitable technique or techniques can be utilized to determine the fall risk value. For example, the controller can be adapted to determine the fall risk value based on a sensor signal generated by the sensor 14. The sensor signal can be based on one or more physiological and/or environmental characteristics detected by the sensor 14. The controller 16 can be further adapted to determine the fall risk value based on other inputs as well. For example, in one or more embodiments, one or more inputs can be provided by one or more of the wearer, the caregiver, and the physician. For example, one or more inputs can be provided by the wearer in response to one or more queries provided, e.g., by the hearing device 12, the caregiver, or the physician.

In one or more embodiments, a postural stability (i.e., displacement of the head of the wearer in three dimensions) of the wearer can be monitored to determine a fall risk value. Any suitable sensor or sensors 14 can be utilized to determine postural stability, e.g., one or more of an accelerometer, gyroscope, microphone, barometer, optical sensor, and bioelectrical sensor. In one or more embodiments, the sensor 14 can include an accelerometer and a gyroscope as the primary sensors for postural balance and fall-risk monitoring and the other sensors can be secondary sensors. For example, a secondary sensor can include a microphone that may be used for detecting footfalls or a fall event. Further, a barometer may be used to detect stair climbing. In addition, an optical sensor may be used for measuring heart rate and other biosignals. A bioelectric sensor may be used for monitoring electro-, cardio-, encephalo-, occulo-, and myograph signals from any location on the head and body of the wearer.

In general, there can be multiple activities and postures during which one may fall down, most commonly walking and standing, transitions between postures such as movement between standing and sitting, etc. Further, there can be identifiable physiological events that precede the fall, such as postural hypotension.

One or more physiological sensors 14 may be employed to identify a "prodrome" of a postural instability. Some possible techniques of using this sensor information for this purpose can be used individually or in combination.

For example, in one or more embodiments, the sensor 14 can include one or more of an accelerometer and a gyroscope. Signals form the sensor 14 can be used to compute and monitor a deviation from a stable position and a velocity with which that takes place. In one or more embodiments, the controller 16 can utilize the signal inputs from the sensor 14 to generate a measure of postural stability. Postural stability can be recorded during normal daily activities, including standing, walking, and climbing stairs. A threshold of normal stability can be established based on clinical postural stability testing or during a user initiated initialization involving one or more of these activities. Measurements in case of a recorded fall can be used to adjust the threshold, if appropriate.

Acceleration of the head of the wearer while walking is complex, with the most prominent feature in the unprocessed accelerometer signal being that of the foot-fall. Adding to this complexity can be stabilization of the head by the neck. Footfall signals may be diminished by neck stabilization but still can be detectable. Vestibular-ocular reflexes can also be measured as the eye will attempt to stabilize the individual's visual field with each step. In one or more embodiments, head oscillation in three dimensions (antero-posterior (AP), lateral, and vertical) can measured. Components of the displacement and the velocity in each dimension can be computed as measures of the postural stability. Although generally correlated and constrained by the body, the head can move relatively independently, which introduces artifacts. To mitigate these artifacts, in one or more embodiments, the velocity and displacement of the head oscillation are computed only when the pitch, yaw and/or roll motions of the head a slower than some predefined thresholds. Artifacts related to head movements may also be mitigated, by the controller, through the integration of sensor inputs of body-worn sensors placed on the chest, trunk, waist, etc. The values can depend upon the speed and type of body movement.

In one or more embodiments, the controller 16 can be adapted to determine the fall risk threshold by measuring a maximum displacement between a longitudinal axis of the wearer and a normal to the earth's surface as a function of time. Further, in one or more embodiments, the controller 16 can be adapted to determine the fall risk threshold by measuring a maximum velocity of displacement between a longitudinal axis of the wearer and a normal to the earth's surface.

Thresholds of safe postural stability or limits of stability can be established by balance testing in a clinical setting or by user-conducted self-directed tests. A fall risk signal or other fall risk output can be generated based on single or multiple threshold crossings.

Parameters of postural stability, i.e., balance metrics, and fall risk values or probabilities can be of interest to one or more of the wearer, caregivers such as the family members, and medical professionals. Balance metrics and fall risk values may be monitored daily and transmitted to various parties. Once a fall risk threshold is exceeded, a fall risk output such as a discrete audio alert may be provided to the user.

In laboratory conditions, head worn IMU sensors can be utilized to characterize small motions (e.g., sway) that can be important for balance evaluation. The orientation of the IMU sensors, however, is highly controlled and well calibrated in the laboratory. In practice, when wearers are wearing two hearing devices, proper alignment of the IMU sensors at each side of the head is desired. Any suitable technique or techniques can be utilized to align the sensor 14 in both left and right hearing devices of the system 10, e.g., the techniques described in U.S. patent application Ser. No. 15/331,230, filed Oct. 21, 2016, and entitled HEAD RELATED TRANSFER FUNCTION INDIVIDUALIZATION FOR HEARING DEVICE. In one or more embodiments, a technique can be utilized to compensate for the orientation mismatch between two hearing devices so that the IMU sensors on both sides of the head can be collaboratively aligned with the head orientation and used to derive postural stability information.

In one or more embodiments, the fall risk value based upon postural stability can be determined by first detecting that the wearer is walking. One or more artifacts from the sensor 14 caused by foot-impact can be filtered out using any suitable technique or techniques. Postural stability can be determined using any suitable technique or techniques. Velocity components of such postural stability can be determined using any suitable technique or techniques. In one or more embodiments, the fall risk value can be based upon walking speed, distance walked, frequency of walks, duration of walks, frequency of successful postural transitions, speed of postural transitions and other activity classifications, and combinations thereof.

A composite sensitivity parameter of the contribution of the sensor 14 (e.g., one or more accelerometers) to the overall fall risk value can be determined using any suitable technique or techniques. In one or more embodiments, the sensitivity of the fall risk value to an amplitude of the postural stability can be determined using, e.g., one or more of a user input after a near-fall event, a balance study, and fall detection. The sensitivity of the fall risk value to the stability velocity at a pre-determined postural stability can be determined using, e.g., one or more user inputs after a near-fall event, a balance study, and fall detection. Further, the sensitivity of the fall risk value to a statistically determined combination of the postural stability and the stability velocity can also be determined.

In one or more embodiments, postural stability, sway velocity and other posture, walking and fall-related information can be routinely transmitted to healthcare professionals. The wearer's posture while standing and walking, actual fall events, and user-indicated near-fall events can also be transmitted to healthcare professionals.

If the fall risk value exceeds the fall risk threshold, then an alert can be sent to one or more of the wearer, caregiver, and medical professional. Such alert can include instructions for how to prevent a fall from occurring.

In one or more embodiments, sensors 14 having one or more accelerometers can be placed in both ears of the wearer. Acceleration of the mid-point between the two ears, as opposed to that of one ear, can be calculated to determine postural stability. Further, false positives of fall detection can be reduced by ensuring both sensors 14 follow the same nominal motion pattern. In addition, head rotation around the vertical axis i.e., the yaw, can also be determined and utilized to calculate the fall risk value.

In one or more embodiments, a short-term estimation model (e.g., model 204 of FIG. 3) can be determined by measuring eye movement of the wearer. For example, the fall prediction system 10 can detect eye movements and compare such eye movements to a baseline to determine whether a vestibular event is occurring that may increase the risk of fall. The sensor 14 of the fall prediction system 10 can include one or more eye movement sensors. In one or more embodiments, the system 10 can also include one or more sensors 14 that can measure head movement of the wearer. Data from such head movement sensors 14 can be utilized to correlate with eye movement sensor data to determine the risk of a fall. Any suitable fall prediction system or device can be utilized to measure eye movement of a wearer, e.g., the devices described in U.S. Pat. No. 9,167,356, issued Oct. 20, 2015, and entitled ELECTROOCULOGRAM AS A CONTROL IN A HEARING ASSISTANCE DEVICE.

Figure 4:
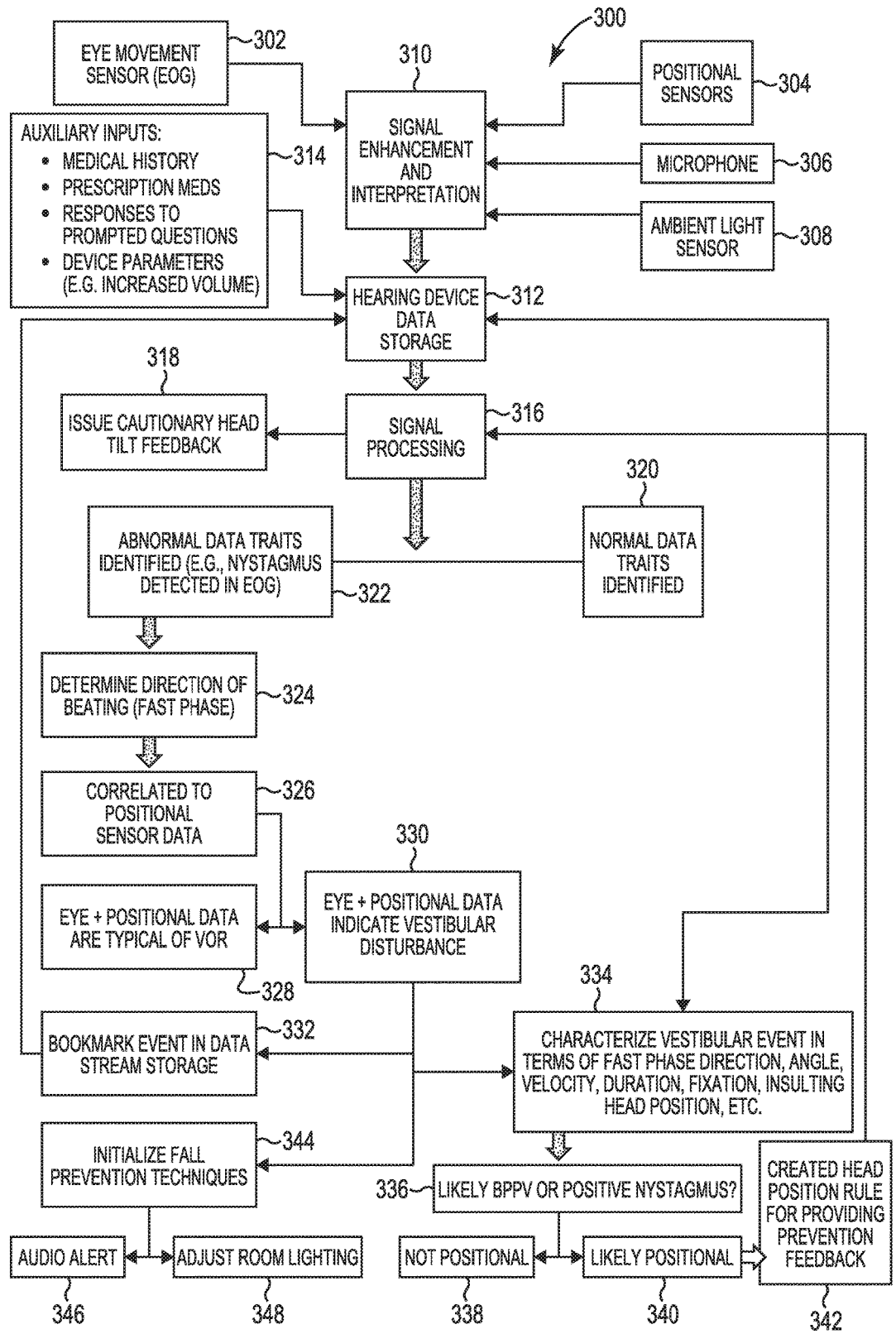
FIG. 4 is a flow chart of another embodiment of a method of utilizing the fall prediction system of FIG. 1.

FIG. 4 is a flow chart of one embodiment of a method 300 for predicting and detecting a fall that utilizes eye movement data. Although described in reference to fall prediction system 10 of FIG. 1, the method 300 can be utilized with any suitable system or systems. In one or more embodiments, data from eye movement sensors 302 (e.g., Electrooculography (EOG) sensors) and positional sensors 304 (collectively sensor 14 of FIG. 1) can be utilized for early detection of peripheral vestibular asymmetry (which generally cause nystagmus and feelings of imbalance/dizziness to occur). Nystagmus is an involuntary oscillation of one or both eyes about one or more axes. The eye movement sensors 302 can allow the system 10 to make one or more of the following determinations: (a) whether or not the nystagmus is typical given the wearer's baseline movement data, (b) whether the wearer's visual pursuits are smooth or otherwise atypical. Other sensors can be utilized with the method 300 to predict and/or detect falls. For example, the system 10 can include at least one of a microphone 306 and an ambient light sensor 308.

In one or more embodiments, the controller 16 can also be adapted to determine the fall risk threshold by first calculating one or more of the direction of visual gaze, the direction of body movement, and the ambient light level, and then inferring the likelihood that the movements of the wearer are adequately coordinated with visual sensory input. For example, an individual is at higher risk for falling when moving backwards, towards a chair, when attempting to sit down, etc. Similarly, an individual is at a greater risk for falling when looking away from their walking path or when the walking path is not well-illuminated. Once a fall risk threshold is exceeded, a fall risk output such as a discrete audio alert may be provided to the user and the ambient light level may be increased for the wearer.

Parallel positional sensors (as in the case of a binaural set of equipped hearing devices or systems) can also be used to detect falls. The use of two separate, but parallel, positional sensors can provide redundancies that can prevent false fall detections (e.g., if the wearer removes or drops the fall prediction systems, the data from the system's axis sensors will not indicate synchronous movements in the same way that they would if being worn during a fall event).

One or more signals from the sensors 302, 304, 306, 308 can be enhanced and interpreted using any suitable technique or techniques at 310. The enhanced signals can be stored using any suitable data storage device at 312. Further, auxiliary inputs 314 such as medical history, prescription medication records, responses to prompted questions by the wearer, and any device parameters such as increased sound volume level of the device can also be stored at 312. For example, manual increases in the volume level of the hearing device 12 enacted by the wearer may indicate that a shift in hearing sensitivity of the wearer may have occurred. Such changes in hearing sensitivity may be clinical indications of Meniere's disease or endolymphatic hydrops.

At 316, any suitable technique or techniques can be utilized to process the signals from the various devices and interpret the auxiliary inputs. In one or more embodiments, the sensor signals are filtered and noise in the signal is rejected. Data from the eye movement sensor 302 and the positional sensors 304 can be analyzed to determine the direction of simultaneous head and eye movements (i.e., determine gaze). A warning based upon this data can be provided to the wearer or caregiver at 318 if such data indicates an imminent fall.

The processed signals can be analyzed to determine normal data traits at 320 using any suitable technique or techniques. Such normal data traits can indicate smooth eye and head movements. Further, at 322, abnormal data traits such as nystagmus can be identified using any suitable technique or techniques. Such abnormal data traits can include abnormal signatures of head and eye movements. Further, nystagmus can be observed in eye movement sensor data. Nystagmus can be identifiable when the wearer's eyes exhibit both a fast movement phase followed by a slow movement phase in the opposite direction of the fast phase. Nystagmus can appear as a pattern of repeated fast phase and slow phase eye movements. Further, the abnormal signatures may include abnormal head movement, which may include rapid movement, detection of free fall or impact, etc.

At 324, the direction of beating (fast phase) of the wearer's eye movements can be determined using any suitable technique or techniques. The eyes can be determined to be beating in one direction (e.g., right or left), in alternating directions (i.e., right and left), or torsional (i.e., in a twisting motion to right or left and either up or down).

The data regarding the direction of beating of the eyes can be correlated to positional sensor data at 326 using any suitable technique or techniques. For example, eye motion data can be analyzed within the context of the measured head movement (i.e., positional data).

At 328, eye movement and positional data indicate that a typical vestibulo-ocular Reflex (VOR). In other words, eye movement and positional data indicate that the wearer's eyes move in opposite angular directions of the head when the wearer is maintaining a steady gaze. In one or more embodiments, the eye movement and positional data indicate typical optokinetic responses, i.e., nystagmus is present when the wearer experiences a rapid velocity (e.g., when looking through the window of a car and watching the trees pass by).

At 330, eye movement and positional data indicate that the wearer is experiencing a vestibular disturbance. Such disturbance can be determined when nystagmus is present when the head is not moving, when the eyes are moving in alternating directions, when the onset of nystagmus follows seconds after a movement of the head (usually when (but not always) the head is tilted upward), or when such nystagmus persists for greater than several seconds.

The event can be bookmarked in data storage at 332 using any suitable technique or techniques. For example, a rolling buffer of data can be kept, and when an event is detected in the data stream, that segment can be recorded and tagged for manual interpretation later. This can include a time window before conditions were observed, which may show data regarding the possible cause of the balance event. This data can be shared with medical professionals such as physicians, audiologists, and physical therapists to assist in rapid differential diagnosis of the wearer.

At 334, the vestibular event can be characterized in terms of, e.g., fast phase direction, angle, velocity, duration, fixation, insulting head position, etc., using any suitable technique or techniques. For example, the detected event can be classified based upon relevant parameters of the detected head and eye movements.

At 336, a determination can be made as to whether a likely Benign Paroxismal Positional Vertigo (BPPV) or positional nystagmus has occurred using any suitable technique or techniques. For example, a determination based upon the classification of parameters can be made to determine whether BPPV or positional nystagmus has occurred.

At 338 a determination is made that the event is not positional in nature. For example, the event is considered to be non-positional if the nystagmus does not occur within about 30 seconds after a head/posture change (i.e., crosses a given threshold to make these determinations).

The event can be determined to be likely positional in nature at 340 using any suitable technique or techniques. For example, the event could be related to BPPV if the nystagmus of the wearer initiates within about 30 seconds after a head/posture change (crosses a given threshold to make these determinations), the nystagmus lasts for less than 60 seconds, and the nystagmus fatigues (i.e., is weakened or absent) if the provoking head position occurs again within a short time frame (minutes). In another example, the event could be related to positional cervicogenic dizziness if the nystagmus of the wearer initiates within about 30 seconds after a head/posture change (crosses a given threshold to make these determinations), the nystagmus lasts minutes to hours; additionally, the wearer or medical history of the wearer may indicate neck pain or injury (e.g., whiplash), headache or lightheadedness, or head-worn sensors may indicate decreases in blood pressure or oxygenation. Further, for example, the event is likely positional in nature if the nystagmus reverses or ceases when the wearer returns to the pre-provocation position.

At 342, if the event is determined to be related to the position of the wearer, then a head position rule can be created for providing prevention feedback to the wearer. For example, if positional nystagmus, cervicogenic dizziness or BPPV are suspected, then the provoking head position/maneuver are identified and stored. A cautionary head tilt feedback warning can be provided to the wearer when the wearer's head is in the undesired position. Further, feedback can be provided to the wearer if the wearer's head moves into the undesired position.

Upon the detection of an abnormal nystagmus disturbance, the system 10 can perform one or more of the following tasks: (a) alert the wearer to prepare for a spell of dizziness (e.g., instruct the wearer to sit down or brace himself so that he do not fall) at 344; (b) alert a caregiver or medical professional via a connected messaging device at 346; (c) log the data from the event to determine the length, regularity, and severity of the disturbance; and (d) adjust the lighting within the environment of the wearer so as to assist the wearer in navigating and visually fixating so as to prevent a future fall at 348. Any suitable technique or techniques can be utilized to terminate such feedback that is provided to the wearer. For example, if a medical professional or virtual therapy guidance system (as describes, e.g., in U.S. patent application Ser. No. 15/589,298) corrects the positionally provoked condition, then the wearer may not need to continue being discouraged from that position (until the next observed instance that may or may not occur again).

Correlated data from both binaural fall prediction systems 10 can be used in assisting the medical diagnosis. For example, short episodes (e.g., 1-2 minutes in duration) that occur following a head tilt can be identified as BPPV. Knowing the direction of head tilt that provokes dizziness (and the subsequent direction of nystagmus beats) would offer even greater diagnostic specificity.

For example, the direction of head tilt and nystagmus could be used to identify the exact semi-circular canal with foreign otoconia causing the peripheral vestibular disruption. Compared to current diagnostic methodology, this determination could be made more accurately and without the need to provoke more symptoms of dizziness from the wearer at a later date.

In one or more embodiments, self-learning can help the system 10 become more useful to the wearer. For example, if certain head movements cause symptoms of dizziness to occur, the system 10 can provide real-time feedback that would discourage the wearer from making those movements. This type of conditioning could help wearers to "learn their limits" until the condition has been treated and resolved. In one or more embodiments, machine learning can determine that the problem no longer exists and terminate the feedback being provided to the wearer.

In a similar way, detection of an episode among individuals who are known to suffer from Meniere's disease could allow the system 10 or a technician to make hearing assistance parameter adjustments. Reduction in hearing sensitivity is commonly a secondary symptom of Meniere's attacks and Endolymphatic hydrops. In these cases, the balance sensors could inform temporary increases in hearing aid gain. In one or more embodiments, these wearers can be given various memory settings with varying levels of amplification to allow for tuning adjustment during episodic fluctuations of hearing sensitivity.

In one or more embodiments, the controller 16 can also be adapted to determine the fall risk threshold by detecting the presence of alternating nystagmus and parameters of postural stability and inferring the level of intoxication of the wearer. For example, the consumption of alcohol or other chemical substances can result in periodic, alternating nystagmus, increased postural instability, and an increased risk for falling. Once a fall risk threshold is exceeded, a fall risk output such as a discrete audio alert may be provided to the wearer and, optionally, another threshold may be used to trigger an action which immobilizes the vehicle of the wearer. To further assist the wearer, during intoxication, the controller may be further adapted to arrange alternative modes of transportation on behalf of the wearer, such as arranging a ride share service pick-up or placing the vehicle into a self-driving mode, when wearer user attempts to operate the vehicle.

Figure 5:
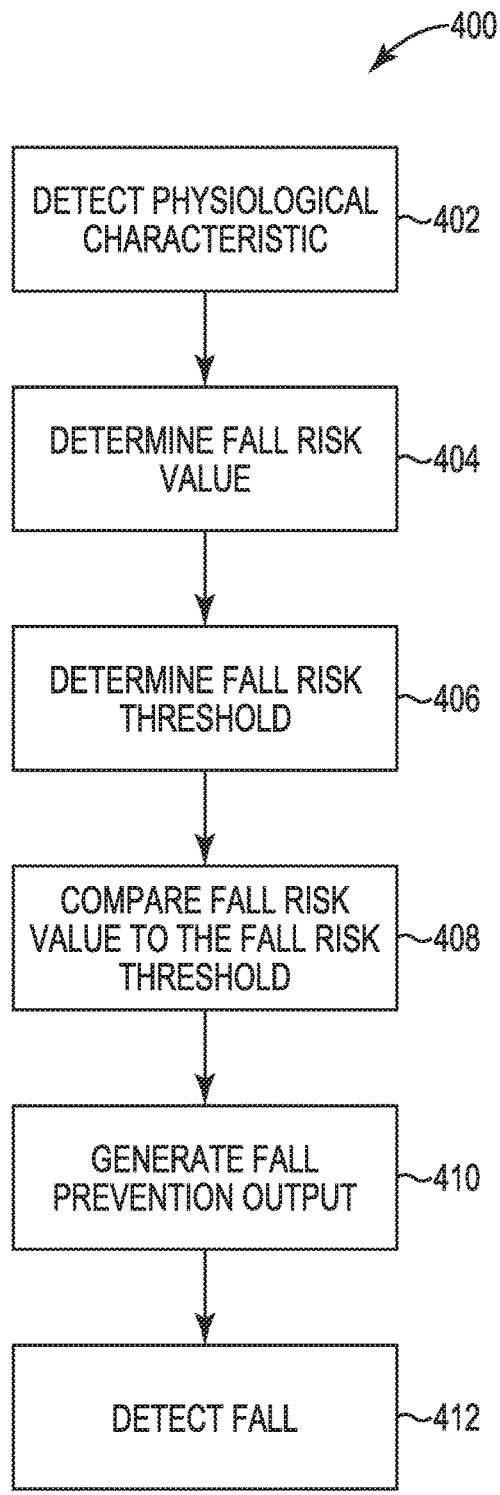
FIG. 5 is a flow chart of another embodiment of a method of utilizing the fall prediction system of FIG. 1.

As mentioned herein, any suitable technique or combination of techniques can be utilized with the fall prediction system 10 to determine the likelihood that the wearer will experience a fall or that the wearer has fallen. For example, FIG. 5 is a schematic flow chart of one embodiment of a method 400 that utilizes the system 10 of FIG. 1, which includes the hearing device 12. Although described in reference to the fall prediction system 10 of FIG. 1, the method 400 can be utilized with any suitable system or device. At 402, the characteristic of a wearer of the fall prediction system 10 can be detected with the sensor 14 using any suitable technique or techniques. Any suitable physiological characteristic of the wearer or the wearer's environment (i.e., an environmental characteristic) can be detected at 402, e.g., a postural stability characteristic. In one or more embodiments, detecting the physiological characteristic includes detecting eye movement of the wearer using a first sensor and a second sensor each operatively connected to the hearing device, and generating an eye movement signal based on the detected eye movement.

A fall risk value based upon the detected characteristic can be determined at 404. Any suitable technique or techniques can be utilized to determine the fall risk value. In one or more embodiments, determining the fall risk value includes detecting head movement of the wearer, generating a head movement signal based on the detected head movement, and comparing an eye movement signal to the head movement signal. At 406 a fall risk threshold can be determined using any suitable technique or techniques. Any suitable fall risk threshold can be determined at 406, e.g., a postural stability threshold.

Further, at 408 the fall risk value can be compared to the fall risk threshold. In one or more embodiments, a fall prevention output can be generated if the fall risk value exceeds the fall risk threshold at 410. The fall prevention output generated at 410 can include any suitable output or outputs. In one or more embodiments, generating the fall prevention output includes transmitting at least one of the physiological characteristic, environmental characteristic, fall risk value, and fall risk threshold to one or more of a caregiver, a medical professional, and the wearer. Further, in one or more embodiments, generating the fall prevention output includes determining a therapy to be delivered to the wearer, and delivering the therapy to the wearer. In or more embodiments, the method 400 can include detecting a fall at 412. Any suitable technique or techniques can be utilized to detect a fall.

All references and publications cited herein are expressly incorporated herein by reference in their entirety into this disclosure, except to the extent they may directly contradict this disclosure. Illustrative embodiments of this disclosure are discussed and reference has been made to possible variations within the scope of this disclosure. These and other variations and modifications in the disclosure will be apparent to those skilled in the art without departing from the scope of the disclosure, and it should be understood that this disclosure is not limited to the illustrative embodiments set forth herein. Accordingly, the disclosure is to be limited only by the claims provided below.

What is claimed is:

1. A fall prediction system, comprising:
a hearing device for a wearer;
a sensor operatively connected to the hearing device and adapted to detect a characteristic of the wearer and generate a sensor signal based on the characteristic, wherein the characteristic comprises at least one of a physiological characteristic and an environmental characteristic of the wearer; and
a controller operatively connected to the hearing device, wherein the controller is adapted to:
determine a fall risk value based on the sensor signal;
compare the fall risk value to a fall risk threshold; and
generate a fall prevention output if the fall risk value exceeds the fall risk threshold;
wherein the controller is further adapted to set the fall risk threshold by at least one of
measuring a maximum displacement between a longitudinal axis of the wearer and a normal to the earth's surface at the location of the wearer as a function of time;
measuring a maximum velocity of displacement between a longitudinal axis of the wearer and a normal to the earth's surface at the location of the wearer as a function of time;
evaluating a medical history of the wearer;
evaluating medications taken by the wearer; or
evaluating one or more inputs provided by the wearer in response to one or more queries.

2. The system of claim 1, wherein the characteristic comprises eye movement of the wearer.

3. The system of claim 1, wherein the characteristic comprises head movement of the wearer.

4. The system of claim 1, wherein the controller is further adapted to determine the fall risk threshold based on one or more settings of the hearing device.

5. The system of claim 1, wherein the fall prevention output comprises at least one of an audible, visual, and tactile signal provided to the wearer.

6. The system of claim 1, wherein the controller is further adapted to detect a fall.

7. The system of claim 1, wherein the hearing device further comprises hearing assistance components disposed within a housing of the hearing device, wherein the hearing assistance components comprise the controller.

8. The system of claim 1, wherein the fall prevention output comprises transmission of at least one of the characteristic, the fall risk value, and the fall risk threshold to one or more of a caregiver, medical professional, or the wearer.

9. A fall prediction system, comprising:
a hearing device for a wearer; a sensor operatively connected to the hearing device and adapted to detect a characteristic of the wearer and generate a sensor signal based on the characteristic, wherein the characteristic comprises at least one of a physiological characteristic and an environmental characteristic of the wearer; and
a controller operatively connected to the hearing device, wherein the controller is adapted to:
determine a fall risk value based on the sensor signal;
compare the fall risk value to a fall risk threshold; and
generate a fall prevention output if the fall risk value exceeds the fall risk threshold;
wherein the controller is further adapted to set the fall risk threshold by evaluating medications taken by the wearer.

10. The method of claim 9, further comprising generating a fall prevention output if the fall risk value exceeds the fall risk threshold.

11. The method of claim 10, further comprising generating a fall prevention output if the fall risk value exceeds the fall risk threshold.

12. The method of claim 10, wherein generating a fall prevention output comprises transmitting at least one of the characteristic, the fall risk value, and the fall risk threshold to one or more of a caregiver, a medical professional, and the wearer.

13. The method of claim 9, wherein the characteristic comprises a postural stability characteristic, and wherein the fall risk threshold comprises a postural stability threshold.

14. The method of claim 9, wherein detecting the characteristic comprises:
detecting eye movement of the wearer using a first sensor and a second sensor each operatively connected to the hearing device; and
generating an eye movement signal based on the detected eye movement.

15. The method of claim 14, wherein determining the fall risk value comprises:
detecting head movement of the wearer;
generating a head movement signal based on the detected head movement; and
comparing the eye movement signal to the head movement signal.

16. A fall prediction system, comprising:
a hearing device for a wearer;
a sensor operatively connected to the hearing device and adapted to detect a characteristic of the wearer and generate a sensor signal based on the characteristic, wherein the characteristic comprises at least one of a physiological characteristic and an environmental characteristic of the wearer; and
a controller operatively connected to the hearing device, wherein the controller is adapted to:
determine a fall risk value based on the sensor signal;
compare the fall risk value to a fall risk threshold; and
generate a fall prevention output if the fall risk value exceeds the fall risk threshold;
wherein the fall prevention output comprises an adjustment of an intensity of light in a room occupied by the wearer.

17. A fall prediction system, comprising:
a hearing device for a wearer;
a sensor operatively connected to the hearing device and adapted to detect a characteristic of the wearer and generate a sensor signal based on the characteristic, wherein the characteristic comprises at least one of a physiological characteristic and an environmental characteristic of the wearer; and
a controller operatively connected to the hearing device, wherein the controller is adapted to:
determine a fall risk value based on the sensor signal;
compare the fall risk value to a fall risk threshold; and
generate a fall prevention output if the fall risk value exceeds the fall risk threshold;
wherein the fall prevention output comprises notifying other devices proximate to the wearer.

18. A fall prediction system, comprising:
a hearing device for a wearer;
a sensor operatively connected to the hearing device and adapted to detect a characteristic of the wearer and generate a sensor signal based on the characteristic, wherein the characteristic comprises at least one of a physiological characteristic and an environmental characteristic of the wearer; and
a controller operatively connected to the hearing device, wherein the controller is adapted to:
determine a fall risk value based on the sensor signal;
compare the fall risk value to a fall risk threshold; and
generate a fall prevention output if the fall risk value exceeds the fall risk threshold;
wherein the fall prevention output comprises notifying other devices proximate to the wearer.

19. A fall prediction system, comprising:
a hearing device for a wearer;
a sensor operatively connected to the hearing device and adapted to detect a characteristic of the wearer and generate a sensor signal based on the characteristic, wherein the characteristic comprises at least one of a physiological characteristic and an environmental characteristic of the wearer; and
a controller operatively connected to the hearing device, wherein the controller is adapted to:
determine a fall risk value based on the sensor signal;
compare the fall risk value to a fall risk threshold; and
generate a fall prevention output if the fall risk value exceeds the fall risk threshold;
wherein the controller is further adapted to set the fall risk threshold by evaluating medications taken by the wearer.

* * * * *

UNITED STATES PATENT AND TRADEMARK OFFICE
CERTIFICATE OF CORRECTION

PATENT NO. : 10,624,559 B2
APPLICATION NO. : 15/858630
DATED : April 21, 2020
INVENTOR(S) : Sourav K. Bhunia et al.

Page 1 of 2

It is certified that error appears in the above-identified patent and that said Letters Patent is hereby corrected as shown below:

On the Title Page

Item (54) and in the Specification at Column 1, Lines 1-2, Title, "FALL PREDICTION SYSTEM AND METHOD OF USING THE SAME" should read --FALL PREDICTION SYSTEM AND METHOD OF USING SAME--

In the Claims

Column 19, Lines 11-26, Claim 9 should read:
--A method, comprising:
detecting a characteristic of a wearer of a fall prediction system with a sensor, wherein the fall prediction system comprises a hearing device, and further wherein the characteristic comprises at least one of a physiological characteristic and an environmental characteristic of the wearer;
determining a fall risk value based on the detected characteristic;
determining a fall risk threshold; and
comparing the fall risk value to the fall risk threshold.--

Column 19, Lines 31-33, Claim 11 should read:
--The method of claim 10, wherein generating a fall prevention output comprises transmitting at least one of the characteristic, the fall risk value, and the fall risk threshold to one or more of a caregiver, a medical professional, and the wearer.--

Column 19, Lines 34-38, Claim 12 should read:
--The method of claim 10, wherein generating a fall prevention output comprises:
determining a therapy to be delivered to the wearer; and
delivering the therapy to the wearer.--

Column 19, Lines 49-61 and Column 20, Lines 1-11, Claim 16 should read:
--A fall prediction system, comprising:
a hearing device for a wearer;

Signed and Sealed this
Twenty-second Day of December, 2020

Andrei Iancu
*Director of the United States Patent and Trademark Office* a first sensor operatively connected to the hearing device and adapted to detect a first characteristic of the wearer and generate a first sensor signal based on the first characteristic, wherein the first characteristic comprises at least one of a physiological characteristic and an environmental characteristic of the wearer;
a second sensor operatively connected to the hearing device and adapted to detect a second characteristic of the wearer and generate a second sensor signal based on the second characteristic; and
a controller operatively connected to the hearing device, wherein the controller is adapted to:
determine a fall risk value based on the first sensor signal and the second sensor signal;
compare the fall risk value to a fall risk threshold; and
generate a fall prevention output if the fall risk value exceeds the fall risk threshold
wherein the first characteristic comprises eye movement of the wearer and the second characteristic comprises head movement of the wearer.--

Column 20, Lines 25 and 26, Claim 17 should read:
--wherein the fail prevention output comprises an adjustment of an intensity of light in a room occupied by the wearer.--